United States Patent [19]

Williams

[11] Patent Number: 4,646,750
[45] Date of Patent: * Mar. 3, 1987

[54] DETECTION OF PULMONARY INFLAMMATION USING BREATH LUMINESCENCE

[76] Inventor: Martin D. Williams, 4317 Accomack Dr., Louisville, Ky. 40222

[*] Notice: The portion of the term of this patent subsequent to Aug. 13, 2002 has been disclaimed.

[21] Appl. No.: 764,344

[22] Filed: Aug. 12, 1985

Related U.S. Application Data

[63] Continuation-in-part of Ser. No. 498,762, May 27, 1983, Pat. No. 4,534,360.

[51] Int. Cl.$^4$ ............................................. G01N 33/10
[52] U.S. Cl. .................................. 128/716; 128/664; 128/665; 128/730; 128/206.29
[58] Field of Search ............... 128/716, 719, 730, 664, 128/665, 666, 206.29, 207.11

[56] References Cited

U.S. PATENT DOCUMENTS

| | | | |
|---|---|---|---|
| 1,395,948 | 11/1921 | Drager. | |
| 2,062,325 | 12/1936 | Manson | 128/141 |
| 2,804,069 | 8/1957 | Schwamm et al. | 128/664 |
| 3,888,630 | 6/1975 | Hoeg | 23/232 |
| 4,534,360 | 8/1985 | Williams | 128/730 |
| 4,576,173 | 3/1986 | Parker et al. | 128/664 |

FOREIGN PATENT DOCUMENTS

| | | | |
|---|---|---|---|
| 618808 | 4/1961 | Canada | 128/207.11 |
| 2630606 | 12/1978 | Fed. Rep. of Germany | 128/665 |
| 2452098 | 11/1980 | France | 128/716 |
| 4129786 | 10/1979 | Japan | 128/716 |
| 735979 | 9/1976 | U.S.S.R. | 128/716 |

OTHER PUBLICATIONS

Szeles, Biothermography in the 8–14 Micron Spectral Region, May 1969, pp. 23–30 of Proceedings of the 7 Annual Biomedical Sciences Instrumentation Symposium on Imagery in Medicine.

Kinsey et al., Endoscopic System for Simultaneous Visual Examination and Electronic Detection of Fluorescence Oct. 1980, pp. 1403–1406 of American Institute of Physics–Rev. Sci. Instrument.

Doiron et al., Fluorescence Bronchoscopy for Dectection of Lung Cancer, Jul. 1979, pp. 27–32 of Chest 1976.

Balchum, O. J., Doiron, D. R., Profio, A. E., and Huth, G. C., (1982)–Fluorescence Bronchoscopy for Localizing Early Bronchial Cancer & Carcinoma in situ, in Recent Results in Cancer Research, vol. 82, pp. 97–120, P. R. Bond, ed., Springer Verlag, Berlin, Heidelberg, and New York.

De Chatelet, L. R. and Shirley, P. S. (1981), Evaluation of Chronic Granulomatous Disease by a Chemiluminescence Assay of Microliter Quantities of Whole Blood, Clinical Chemistry, 27, 1739–1941.

Krotozynski, B., Gabriel, G., and O'Neill, H., Claudio, M. P. A., (1977), Characterization of Human Expired Air: A Promising Investigative and Diagnostic Techique, Journal of Chromatographic Science, 15, 239–244.

List Continued on next page.

*Primary Examiner*—Edward M. Coven
*Attorney, Agent, or Firm*—Howson & Howson

[57] ABSTRACT

Subjects may be screened for possible lung inflammation by a breath luminescence measurement apparatus and technique. The apparatus comprises a photon counter with special provisions for the exclusion of light from sources other than the patient's breath. A special light exclusion mask is used together with tortuous breath exhaust passages to exclude external light. A gauze plug in the breathing tube excludes light emitted by the patient's mouth tissues. Luminescence measurements higher than normal for healthy persons of the same age as the patient are indicative of lung inflammation.

7 Claims, 15 Drawing Figures

OTHER PUBLICATIONS

Williams, M. D., Leigh Jr., J. S. & Chance, B., Hydrogen Peroxide in Human Breath and Its Probable Role in Spontaneous Breath Luminescence, Annals New York Academy of Sciences (May 28, 1982), pp. 478–483.

Williams, M. D., Chance, B. and Leigh, Jr., J. S., Spontaneous Ultraviolet Chemiluminescence of Human Breath in Situ, VII Int. Biophysics Congress and II Pan-American Biochemistry Congress Program and Abstracts, Mexico City, MX, p. 104 (Sep. 1981).

Williams, M. D., D. A. Rodriguez, J. S. Leigh, Jr. and B. Chance, Spontaneous Luminescence of Human Breath-Correlation of Luminescence Intensity and Hydrogen Peroxide Content, Biophysical Journal 37, 83a, Abstracts of the 26th Ann. Mtg. of the Biophysical Society, Boston, MA, p. 83a (Feb. 1982).

Williams, M. D., and Chance, B., Optical Spectrum, Decay Time, Temporal Distribution and Correlation with Peroxide of Human Breath Spontaneous Chemiluminescence, Biophysics Journal (1983).

Williams, M. D., and Chance B., Spontaneous Chemiluminescence of Human Breath, Spectrum, Lifetime, Temporal Distribution, and Correlation with Peroxide, The Journal of Biological Chemistry (Mar. 25, 1983), pp. 3628–3631.

Williams, Letter, Science (12 Feb. 1982) vol. 215, No. 4534, p. 745, Williams, M. D., Breath-Lung Luminescence, The Gerontologist 22, 171 (Abstract No. 141) (Nov. 1982).

Doiron et al., "Fluorescence Bronchoscopy . . . ", Chest 76:1, Jul. 1979, pp. 27–32.

Kinsey and Cortese, "Endoscopic System for Simultaneous Visual Examination and Electronic Detection of Fluorescence", Rev. Sci. Instrum, Oct. 1980, pp. 1403–1406.

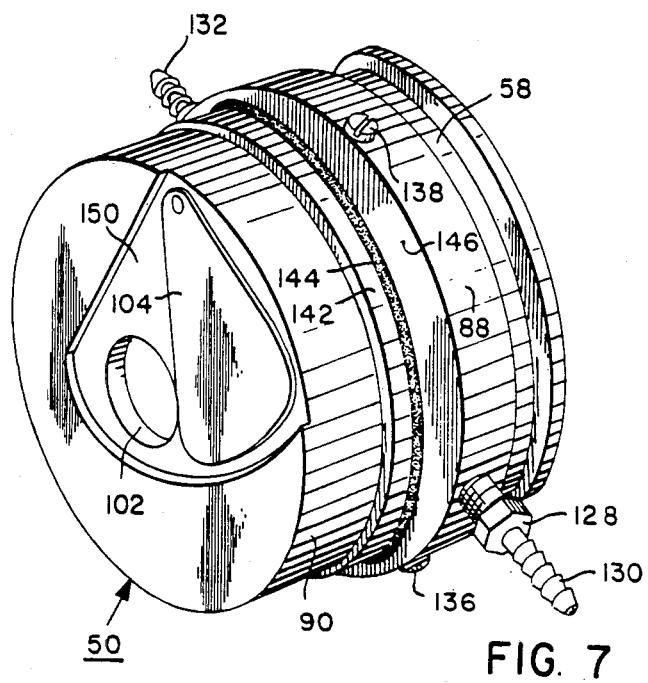

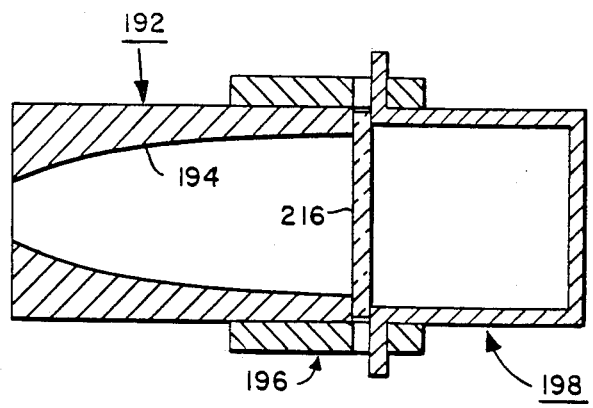
FIG. 12
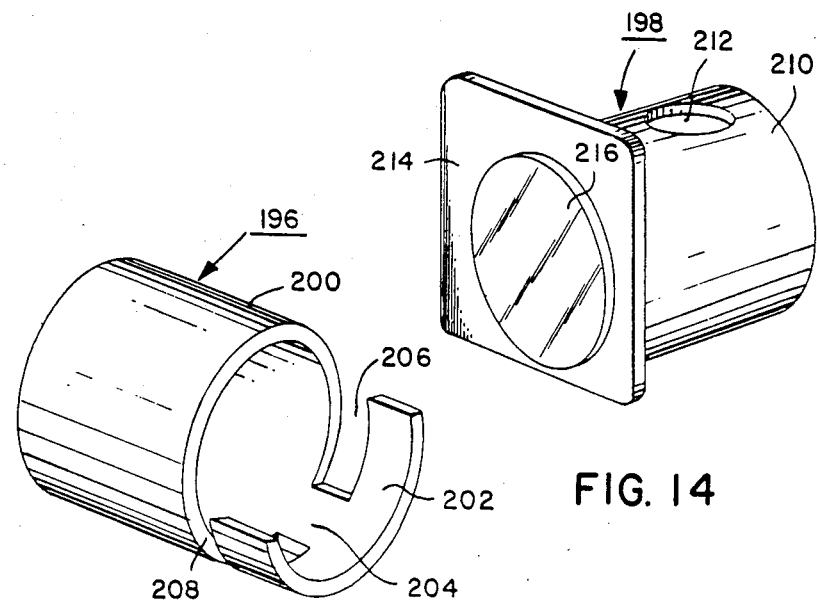
FIG. 14
FIG. 13

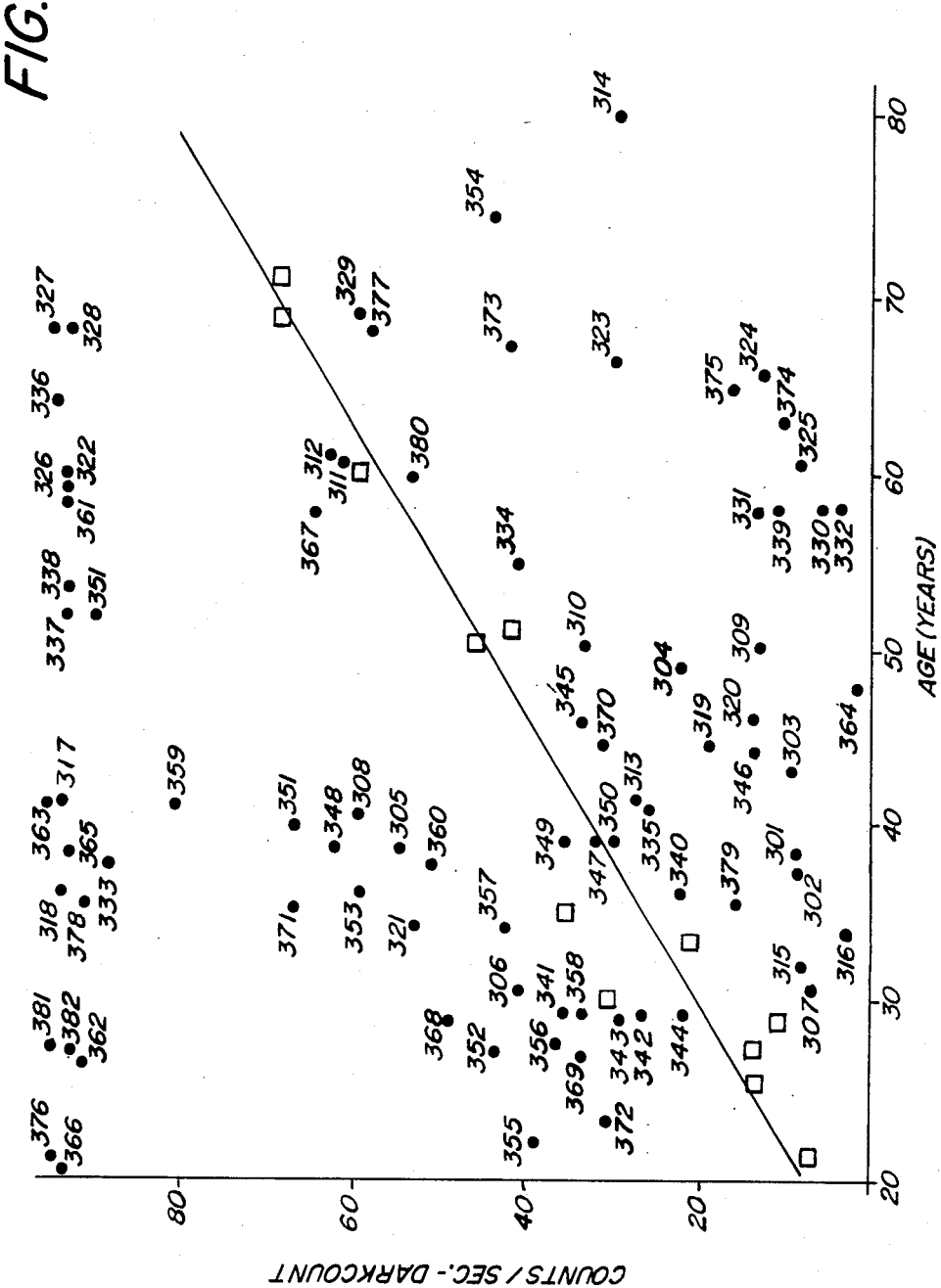

DETECTION OF PULMONARY INFLAMMATION USING BREATH LUMINESCENCE

CROSS-REFERENCE TO RELATED APPLICATION

This application is a continuation-in-part of my copending application, Ser. No. 498,762, filed May 27, 1983, now U.S. Pat. No. 4,534,360, dated Aug. 13, 1985.

BRIEF SUMMARY OF THE INVENTION

This invention relates to diagnostic methods, and particularly to a method for detecting pulmonary inflammation.

The invention uses non-invasive techniques, and therefore is useful in preliminary screening of candidates for more extensive diagnostic tests or for confirming prior diagnoses. With further development, the invention may eventually replace some of the present diagnostic techniques.

Existing techniques for the detection of lung diseases include X-ray examination, bronchoscopy, tissue biopsy, blood gas analysis, spirometry, auscultation, and plethysmography. Existing techniques have various disadvantages. X-ray examination, bronchoscopy, biopsy, blood gas analysis, spirometry and plethysmography are all expensive to perform. X-ray examinations, bronchoscopy and biopsy are also hazardous to a significant degree. Blood gas analysis, spirometry, plethysmography and auscultation are general tests which are less reliable than X-ray examination, bronchoscopy and tissue biopsy. Some of the other currently used techniques are also not very effective.

The general object of the present invention is to overcome the aforementioned disadvantages of current techniques. Specifically, it is an object of the invention to provide for the detection of lung inflammation low-cost, portable equipment which is structurally simple and easy to maintain. It is also an object of the invention to provide for accurate, reliable, rapid and easily performed tests which can be carried out without any patient discomfort. Another object of the invention is to provide a technique and apparatus which is capable of detecting inflammatory lung conditions in their early stages in a large percentage of patients. Most significantly, it is an object of the invention to provide a detection technique which is non-invasive and not hazardous to the patient or to medical personnel.

In my previous application which is about to issue as U.S. Pat. No. 4,534,360, I disclosed that human breath luminescence has utility in the detection of lung cancer, and in particular that lung cancer tends to reduce breath luminescence, so that if the measured breath luminescence for a particular subject falls below a preestablished standard for normal persons of the same age as the subject, cancer should be suspected and further diagnostic tests should be performed.

I have now discovered that the measurement of human breath luminescence has utility in the detection of inflammatory diseases of the lung such as sarcoidosis, asthma, pneumonia, etc. In the case of inflammatory conditions, breath luminescence measurements for a particular patient, tend to fall above, rather than below, the normal level for healthy persons of the same age as the patient. In accordance with the invention, inflammatory lung conditions in a human patient are detected by the steps of measuring the quantity of light spontaneously emitted by the breath of the patient, and comparing the quantity of light so measured with a preestablished standard for persons of the same age as the patient who are free of inflammation. If the quantity of light emitted by the patient's breath is substantially above the preestablished standard, the patient is considered a candidate for further diagnostic testing.

The apparatus used in accordance with the invention for detection of inflammatory lung conditions by measuring human breath luminescence comprises a housing, a photosensitive detector within the housing, a breath tube of a size to fit the patient's mouth, the breath tube being arranged to conduct the patient's breath to an exposure location such that luminescence in the patient's breath can be detected by the photosensitive detector, and means providing a path for exhaustion of the patient's breath from the exposure location. Provision is made for excluding, from the photosensitive detector, light from sources other than the patient's breath. The light excluding means includes a light-impermeable mask surrounding the breath tube, attached to the housing, and attachable to the patient's face.

The mask comprises a sheet of flexible, light-impermeable material formed to provide a tubular section having a first opening at one end for attachment to the housing and a second opening at its other end for connection to the face of the patient. The tubular section surrounds the breath tube. A pair of flaps extend from opposite sides of the second opening and are of sufficient length to extend to the rear of the patient's head. These flaps have means for removably securing the flaps together at the rear of the patient's head. Along the lower edges of the flaps, means are provided for removably securing the lower edges of the flaps together underneath the patient's chin. Pads are provided at the locations at which the upper edges of the flaps meet the second opening of the tubular section of the mask. These pads are positioned to occupy the space between the flaps and sides of the patient's nose. The mask is effective to exclude external sources of light from the highly sensitive photodetector so that the photodetector can respond reliably to the very weak luminescence of the patient's breath.

The measuring apparatus of the invention can be used not only for the measurement of breath luminescence, but also for the measurement of luminescence of internal tissue by means of a light-conducting endoscope, and for the measurement of luminescence of various samples. The measuring apparatus is provided with multiple adapters for the measurement of breath luminescence, internal tissue luminescence and sample luminescence.

Additional advantages and objects of the invention will be apparent from the following detailed description when read in conjunction with the drawings.

DESCRIPTION OF THE DRAWINGS

FIG. 7 is an oblique perspective view of the breath collection adapter, showing the underside thereof and the end thereof which faces the photomultiplier;

FIG. 8 is an elevational view of the bayonet locking ring;

FIG. 12 is a cross-sectional view of a special adapter for use in measuring luminescence of samples;

FIG. 13 is a perspective view of a receiver which constitutes part of the assembly of FIG. 12;

FIG. 14 is a perspective view of a sample holder which constitutes another part of the assembly of FIG. 12; and FIG. 15 is a plot illustrating the manner in which the apparatus is used in the detection of inflammatory lung conditions.

DETAILED DESCRIPTION

The Breath Luminescence Detector

Figure 1:
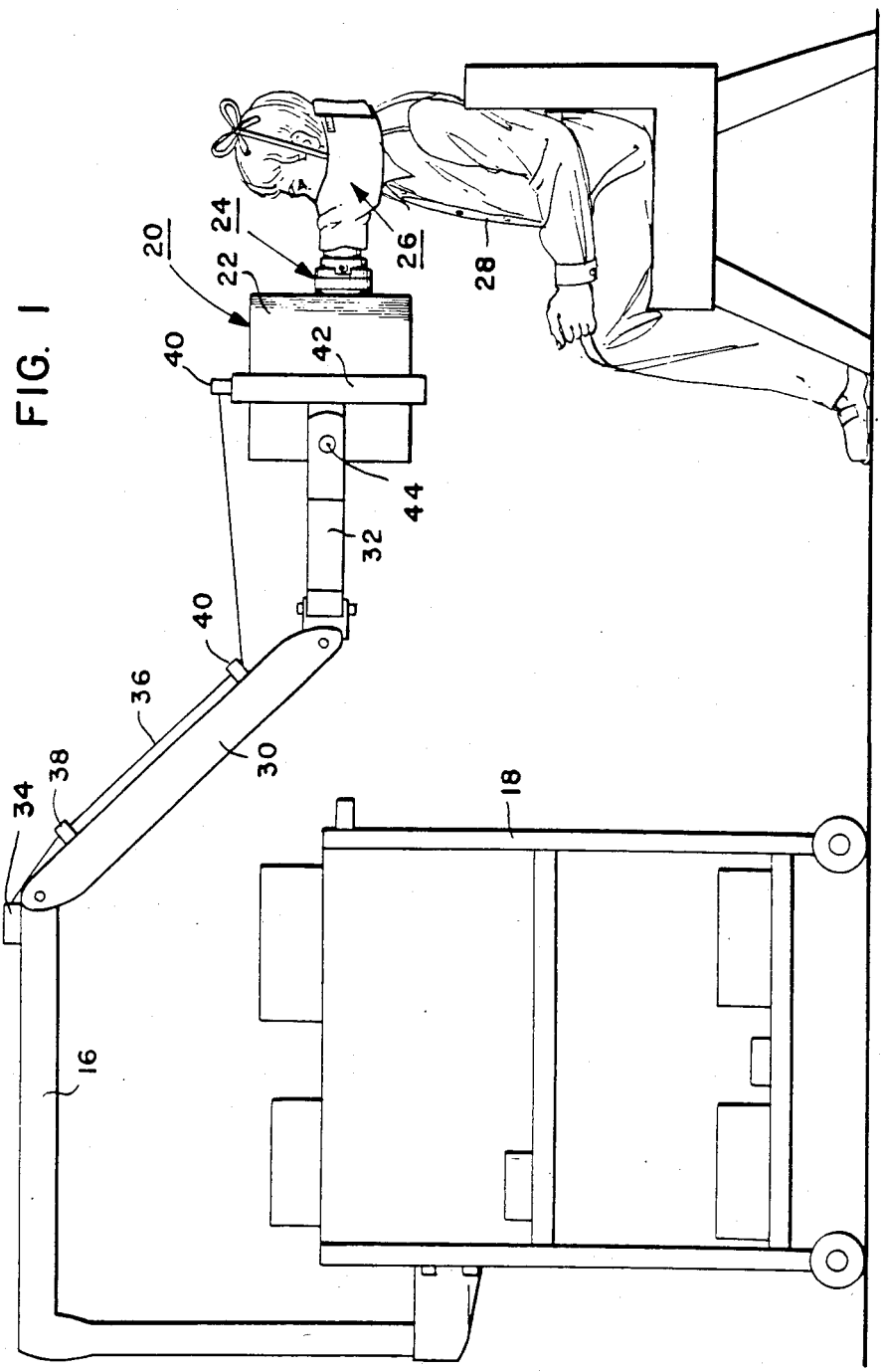
FIG. 1 is an elevational view of the breath luminescence measurement apparatus in accordance with the invention, showing its supporting boom and its relationship to the patient.

As shown in FIG. 1, the apparatus includes a boom 16 supported on a movable cart 18. The cart holds a power supply as well as instrumentation and controls for the light-measuring instrument generally indicated at 20. Instrument 20 includes a housing 22 containing a photomultiplier tube or other suitable highly sensitive luminescence detector together with thermoelectric (Peltier) cooling apparatus. Attached to housing 22 is an adapter assembly 24 used to deliver a patient's breath to the vicinity of the photomultiplier tube. A light exclusion mask 26 is connected to adapter assembly 24, and is wrapped around the face of a patient 28 in order to prevent light originating in external sources from interfering with the measurement of the patient's breath luminescence.

Arm 30 is pivoted to boom 16 and moves in a vertical plane. Yoke 32 connects instrument 20 to the lower end of arm 32, and is pivotable horizontally. A constant-force spring in housing 34 is connected to a wire 36 which extends through guides 38 and 41 on arm 30 to an anchor 40 on an instrument housing support bracket 42. Bracket 42 is pivoted for tilting in a vertical plane by a pivot 44 through which it is connected to yoke 32.

Figure 2:
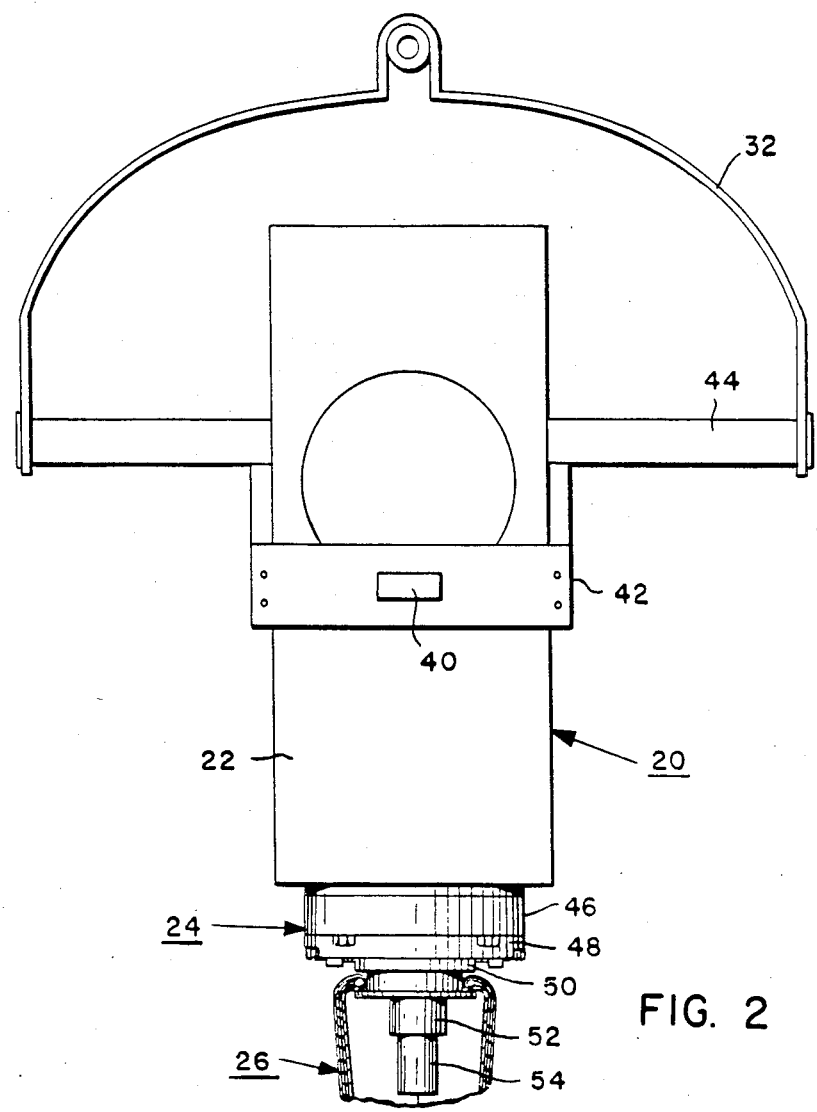
FIG. 2 is a top plan view of a photomultiplier and thermoelectric cooler housing, also showing the breath collector assembly.

The instrument 20 and its supporting yoke 32 are shown in plan view in FIG. 2. The adapter assembly 24 comprises a spacer ring 46, which is bolted to a flange on housing 22. Secured to the spacer ring is a bayonet locking ring 48. An adapter 50 is removably secured to the locking ring and provides a means for attachment of the light exclusion mask 26 to the instrument as well as a support for a metal breath tube adapter 52 which, in turn, receives a disposable breath tube 54. The disposable breath tube can be made of cardboard, plastic or any other suitable material.

Figure 3:
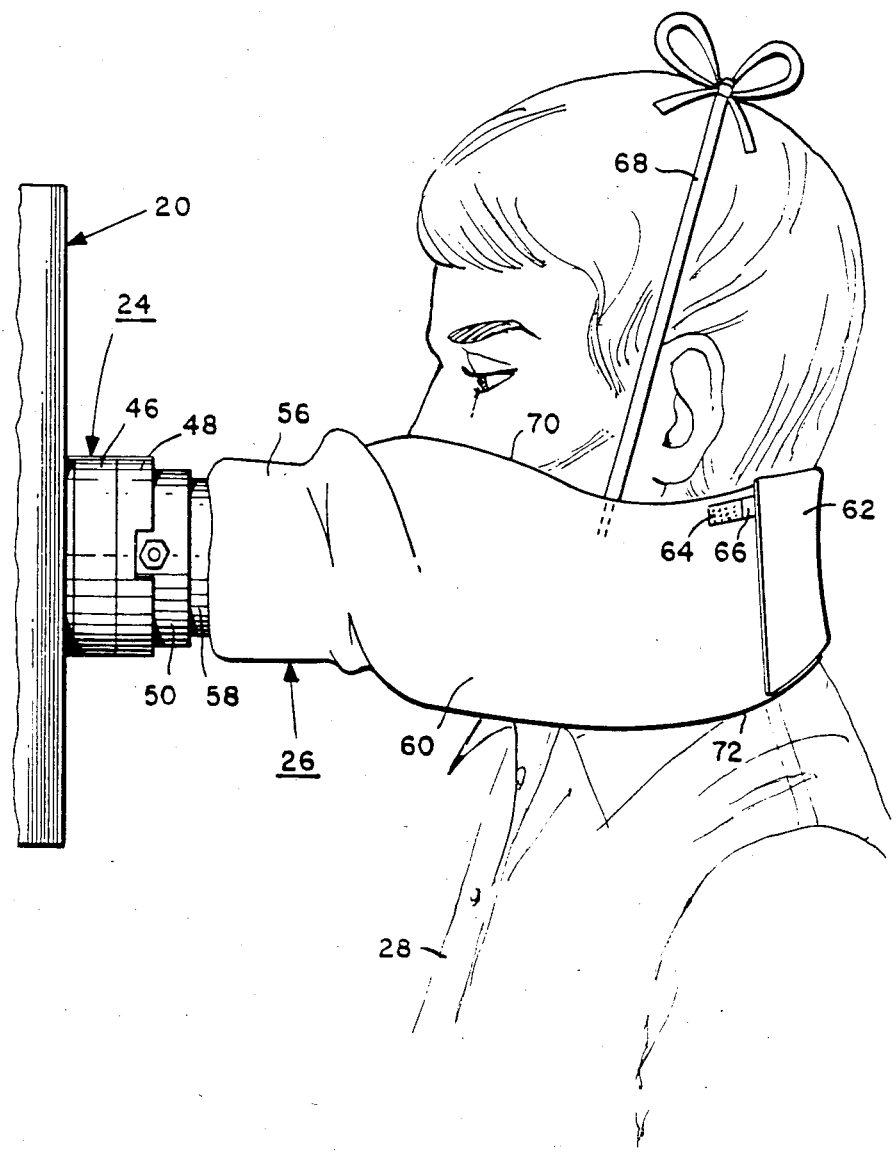
FIG. 3 is an elevational view showing the manner in which the light exclusion mask is affixed to the patient and to the breath collector assembly.

As shown in FIG. 3, mask 26 comprises a tubular section 56, one end of which is drawn tightly into channel 58 of adapter 50 by means of a drawstring (not shown in FIG. 3). Tubular section 56 surrounds the breath tube and the breath tube adapter as shown in FIG. 2, and extends to the patient's face. A flap 60 extends about the left-hand side of the patient's face. A similar flap 62 extends about the right-hand side of the patient's face and is secured to flap 60 by VELCRO press-to-adhere strip fasteners 64 and 66. A band 68, tied over the top of the patient's head, supports the mask at the proper height.

When fitted to the patient, the flaps of the mask provide an upper opening 70 and a lower opening 72, the lower opening accommodating the patient's neck, and the upper opening extending about the patient's face approximately at nose level. The mask can either fit over the patient's nose as shown in FIG. 3, or can be fitted so that the patient's nose is outside the mask.

The flaps are secured together underneath the patient's chin by additional VELCRO fasteners (not shown in FIG. 3) to insure against the entry of external light from below.

Figure 4:
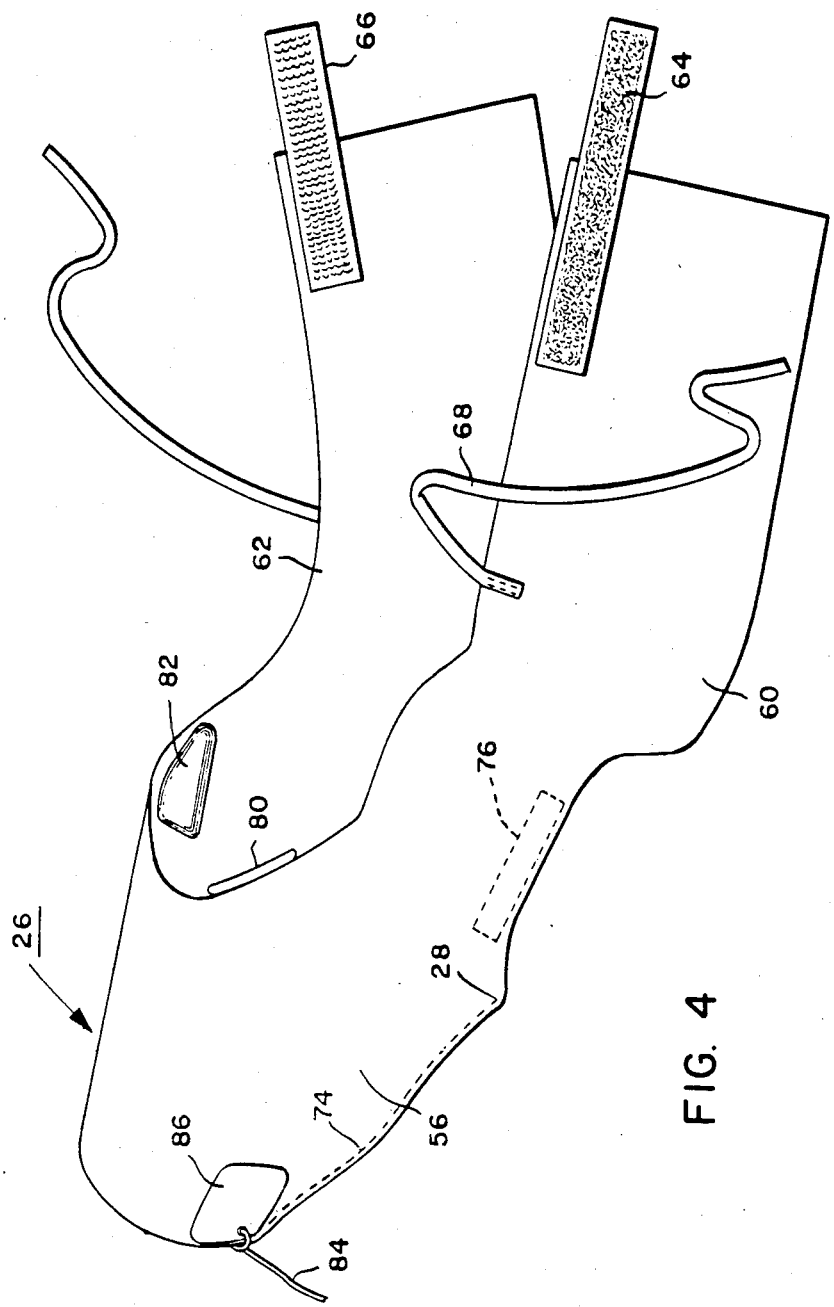
FIG. 4 is a perspective view of the light exclusion mask.

Mask details are shown in FIG. 4. Tubular section 56 is formed by sewing along a seam 74. Flaps 60 and 62 extend rearwardly from opposite sides of tubular section 56. A VELCRO strip 76 on the inside of flap 60 along its lower edge extends rearwardly from the approximate location of the end 78 of seam 74, and cooperates with a corresponding VELCRO strip (not shown) along the lower edge of flap 62 to provide an openable closure underneath the patient's chin. Pads are provided at 80 and 82 to prevent light from entering tubular section 56 of the mask through spaces at the sides of the patient's nose or cheeks. These pads are preferably cotton-filled fabric, and are located along the upper edges of flaps 60 and 62 respectively adjacent to the rear opening of section 56. A drawstring 84 is preferably a length of stranded metal wire which extends through a passage formed at the instrument end of tubular section 56. Reinforcement patches, one of which is shown at 86, are provided on opposite sides of the mask. Drawstring 84 is tied when the mask is fitted onto channel 58 (FIG. 3) of adapter 50.

Figure 6:
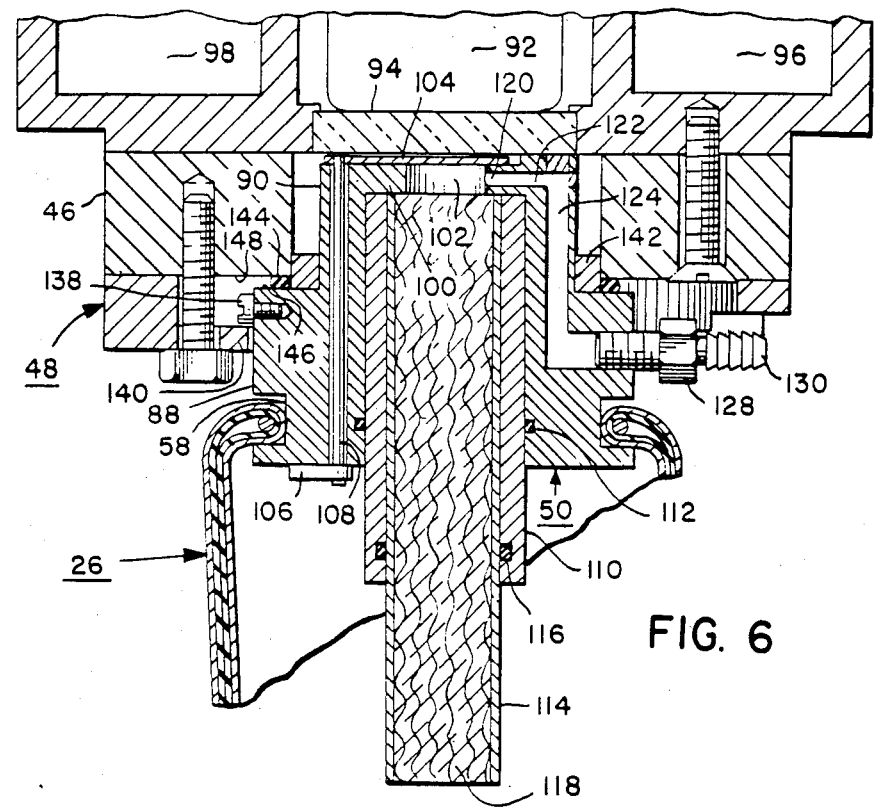
FIG. 6 is a sectional view taken on the surface 6—6 of FIG. 5, showing details of the breath collection adapter and the manner in which it is secured, by a bayonet locking ring, to the housing for the photomultiplier and thermoelectric cooler.

Mask 26, as shown in FIG. 6, is formed from two layers of black, rubberized kettle cloth folded so that the rubberized sides face each other.

Figure 5:
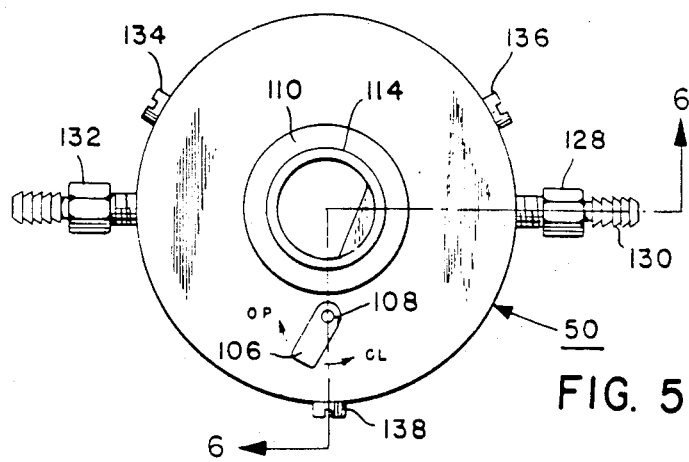
FIG. 5 is a front elevation of a breath collection adapter, also showing a breathing tube adapter and a breathing tube.

Referring to FIGS. 5 and 6, adapter 50 comprises a large cylindrical section 88 having a channel 58 for securing the end of the mask, and a smaller diameter cylindrical section 90 which extends into the opening in spacer ring 46. Photomultiplier tube 92, which serves as a photon counter, is exposed through a quartz window 94. Thermoelectric cooling apparatus is provided in spaces 96 and 98. End wall 100 of cylindrical section 90 is provided with an opening 102 closable by a shutter 104 which is controlled by handle 106 through rod 108. The shutter is closed when a dark count is being taken, and is opened for breath luminescence detection. Adapter 50 can be made of metal, synthetic resin, or any of a wide variety of suitable materials. "DELRIN", a homopolymer acetal resin is an example of a suitable material.

A metal breath tube adapter 110 fits into the cylindrical interior of adapter 50, and is held in place frictionally by O-ring 112. A breath tube 114 extends into tube 110, and is similarly held frictionally by O-ring 116. Breath tube 114 is a disposable tube made of plastic, cardboard or other suitable material. Tube 114 is filled with a plug of cotton gauze 118, the purpose of which is to prevent the photomultiplier tube from receiving light generated by the patient's mouth tissues.

Opening 102 in end wall 100 of adapter 50 has a transverse opening 120 which connects through a radial passage 122 to an axial passage 124. Axial passage 124 connects to another radial passage 126 into which is threaded a fitting 128 having a nipple 130 for the optional connection of a length of rubber tubing (not shown). The tubing can be used to control restriction of air flow through the passages. A similar set of passages (not shown) leads to fitting 132 (FIG. 5) on the opposite side of adapter 50. These passages provide a tortuous outlet for the flow of air so that, as the patient breathes into breath tube 114, air is allowed to flow outwardly from the adapter without the entry of light from external sources. The mask and the tortuous passages together serve to exclude all light from external sources. The gauze plug 118 excludes light generated by the patient's mouth tissues. Thus, the mask, the tortuous passages and the gauze plug together exclude light from all sources other than the patient's breath itself.

Adapter 50 is locked into bayonet ring 48 by the engagement of screw heads 134, 136 and 138 (FIG. 5) with overhanging parts, including part 140, of the bayonet locking ring (FIG. 6). As shown in FIG. 6, a metal ring 142, surrounding section 90 of adapter 50, centers the adapter in the opening of spacer ring 46, and also positions a large-diameter rubber O-ring 144 so that it can be clamped between face 146 of adapter section 88 and face 148 of spacer 46.

FIG. 7 shows the overall structure of adapter 50, including a recess 150 for accommodating shutter 104 and thereby preventing shutter 104 from being pinched between the end wall of adapter 50 and quartz window 94 (FIG. 6).

Bayonet locking ring 48 is shown in FIG. 8. Ring 48 is a metal ring having inwardly projecting overhanging parts 140 and 152 separated from each other by gaps 152 and 154. Bolt holes are provided at 156, 158 and 160, and recesses are provided in the overhanging parts at 162 and 164.

Gaps 153 and 154 accommodate fittings 128 and 132 (FIG. 7). Referring to FIGS. 5 and 8, in the installation of adapter 50 in locking ring 48, screw head 138 enters recess 162, and screw head 134 enters recess 164. Screw head 136 enters gap 153. The adapter, as viewed in FIG. 5, is rotated counterclockwise so that the machine screw heads move behind overhanging parts 140 and 152. This rotating motion locks the adapter in place, and at the same time compresses O-ring 144 axially (FIG. 6).

The Endoscope Adapter

Figure 10:
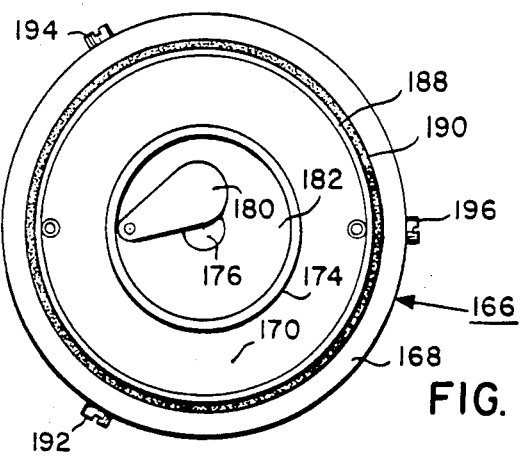
FIG. 10 is an elevational view of the side of the adapter of FIG. 9 which faces the photomultiplier.
Figure 9:
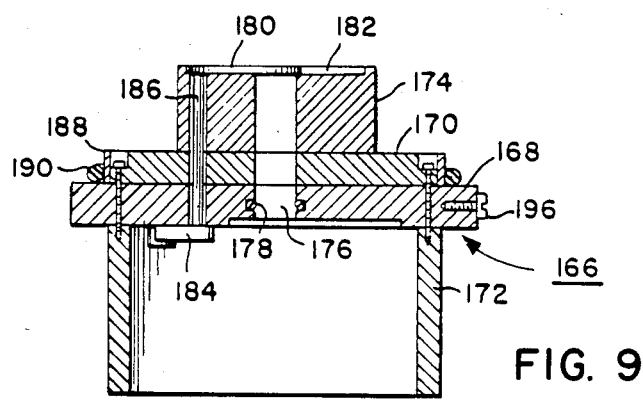
FIG. 9 is a cross-sectional view of a special adapter for use with a flexible, light-conducting tube of an endoscopic device.
Figure 11:
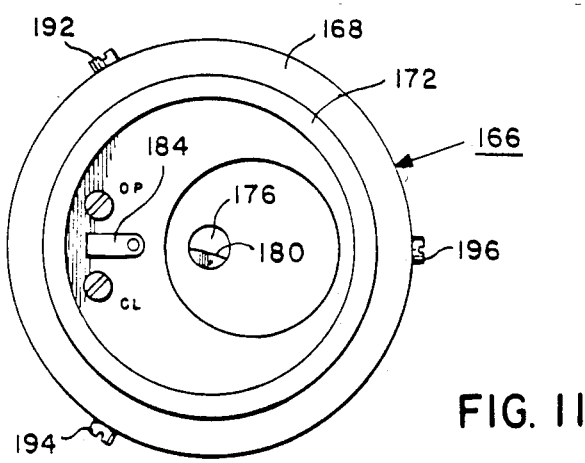
FIG. 11 is an elevational view of the opposite side of the adapter of FIG. 9.

FIGS. 9, 10 and 11 illustrate an adapter 166, which can be used as an alternative to adapter 50, for the measurement of internal tissue luminescence by the use of an endoscopic device such as a bronchoscope having a flexible, light-transmitting fiberoptic cable. In the use of an endoscopic device for detection of luminescence, the optional fibers which are normally used for illustration of internal organs, are used instead to conduct light in the reverse direction from internal organs to the detection apparatus.

Adapter 166 comprises a plate 168 and a plate 170, which is secured to plate 168 by screws. Two screws are threaded into the end of a ring 172 on the opposite side of plate 168. Ring 172 facilitates handling of the adapter, allowing it to be grasped and rotated for insertion and removal from the bayonet locking ring of FIG. 8. Elements 170, 174 and 168 can be machined or molded as a unit if desired. A cylinder 174 is secured to plate 170. A cylindrical passage 176 extends through plates 168 and 170 and cylinder 174. This passage receives a termination fitting on the fiberoptic cable, and is provided with an O-ring 178 for holding the cable termination fitting frictionally. A shutter 180, in a recess 182 in the end face of cylinder 174, is controlled by an operating handle 184 through control rod 186. This shutter is used to obtain a dark count. A ring 188 surrounds plate 170, and a large-diameter O-ring, corresponding to O-ring 144 in FIGS. 6 and 7, surrounds ring 188.

The adapter of FIGS. 9, 10 and 11 can be substituted for the adapter of FIGS. 6 and 7 whenever it is desired to measure luminescence transmitted through a cable from an endoscope or similar device. Adapter 166 (FIG. 9) fits into the locking ring in the same manner as does adapter 50 as shown in FIG. 6.

The Sample Measurement Adapter

FIGS. 12, 13 and 14 illustrate an adapter which permits the photomultiplier to be used for measuring the luminescence of small samples of various substances. The adapter comprises an ideal light collector 192 or other adapter suitable for fitting the sample holder and conducting light to the detector. The ideal light collector is in the form of a tube having a cylindrical exterior surface and a specially curved reflective interior surface 194. Collector 192 fits into adapter 50 (FIG. 6) and has the same exterior diameter as breath tube adapter 110, so that it is held in adapter 50 frictionally by O-ring 112. A receiver 196 fits onto collector 192, and holds a sample holder 198.

As shown in FIG. 13, receiver 196 has a cylindrical section 200, and a semi-circular section 202 connected to section 200 by a connecting element 204 so that slots are provided at 206 and 208.

As shown in FIG. 14, sample holder 198 comprises a hollow cylindrical container 210 having an access opening 212, and having at one of its ends a flange 214 with a light-transmitting quartz window 216. Flange 214 of the sample holder fits into slots 206 and 208 of receiver 196.

The sample holder can be readily removed from and replaced in the receiver slots for the successive measurements of the luminescence of different samples.

Operation Of The Breath Luminescence Detector

A wad of black velvet cloth is normally kept in breathing tube adapter 110 (FIGS. 5 and 6) when the apparatus is not in use and during the establishment of the dark count for the photomultiplier.

The photomultiplier output is delivered to a counter through an amplifier and a window discriminator which are situated on the cart in FIG. 1. At the start of operation, the discriminator is set, and the thermoelectric cooler is activated. When the temperature of the photomultiplier reaches a predetermined intermediate level (e.g. 10° C.), as indicated by a temperature sensor, the photomultiplier high voltage supply is switched on and adjusted to a predetermined level. The amplifier, discriminator and counter are then switched on. When the final temperature is reached (typically −25° C.), the count rate is checked. When the count rate varies within a narrow preestablished range, e.g. between 20 and 40 counts per second, the apparatus is ready for making measurements.

A dark count is established by averaging the counts for three successive one minute intervals. The determination of the dark count is carried out with the room dimly lit, the shutter closed and with the velvet wad in place and the adapter covered with a hood.

Subjects are instructed not to smoke on the day of the measurement, and to sleep for at least seven hours the night before. Subjects are instructed not to eat heavy meals or use alcohol on the day of the measurement. Patients using glucocorticosteriods are not tested, as they can be expected to give unreliable low breath luminescence readings. Subjects are asked to refrain from vigorous exercise, drugs or medication, and vitamins A, B or E for twenty-four hours prior to the measurement.

The patient is seated as shown in FIG. 1, and is coached to inhale through his nose and exhale through his mouth into the breathing tube. The velvet cloth is removed from the breath tube adapter and a new breathing tube 114 is substituted for it as shown in FIG. 6. The mask is gathered toward the instrument to allow the patient to see the breathing tube. The room is darkened, and shutter 104 is opened. The patient is instructed to put his lips tightly around the breathing tube, and to inhale through his nose and exhale through his mouth. The mask is then fastened behind the patient's head as shown in FIG. 3, and band 68 knotted over the patient's head if necessary in order to support the mask. The mask may be secured so that the patient's nose is inside the mask as shown in FIG. 3 or so that the patient's nose is outside the mask. In either event, the mask must fit the patient's face tightly. The VELCRO fastener at the bottom must not be fastened all the way to the subject's neck because if it is fastened all the way to the neck, it may interfere with proper breathing. The detection apparatus on the end of the boom is moved to a height and attitude to permit the patient to assume a comfortable posture. It is also possible to provide an adjustable power chair for the patient. For proper measurement of breath luminescence, it is important that the patient's posture be comfortable so that his head is not bent back but is slightly tilted down. The patient's shoulders should not be hunched.

The room is darkened, and with the shutter open, two successive one minute counts are taken. During the measurement, the patient is repeatedly asked to continue inhaling through his nose and exhaling through his mouth into the breathing tube as normally as possible. Following the measurement, the mask is detached from the patient, and draped over the end of the breathing tube after the shutter is closed. The breathing tube is removed and discarded, and the black velvet cloth is reinserted into the breathing tube adapter until the next measurement takes place. During a series of measurements, dark counts are repeated as frequently as possible.

Total counts obtained during patient measurement, and dark counts are converted to counts per second. The dark counts closest in time to each particular patient measurement are averaged and subtracted from the average count rate for the patient. If the count rate for the particular patient is lower than the norm for healthy, rested, non-smokers of the same age of the patient, further assessment of the patient's lungs for possible cancer is indicated. If, on the other hand, the count rate for the patient is higher than the norm. then possible inflammatory disease is indicated.

In my experiments, a control normal was established from a population of normal subjects who did not smoke, were not aware of any acute or chronic pulmonary problems, and had no history of asthma, bronchitis, bronchiectasis or tuberculosis. They had not used alcohol or medication for at least twenty-four hours, and had not had a large or unusual meal for at least eight hours. They had not taken vitamins A, B or E within twelve hours. Each subject had at least seven hours of sleep in each of the prior two nights, and did not engage in regular vigorous athletics. In my experiments, the age and count rates for the subjects used to establish the control normal are indicated by open squares in FIG. 15, and the control normal is indicated by the sloping straight line. In FIG. 15, the abscissa represents the age of patients and control subjects, and the ordinate represents the average one minute count less the average one minute dark count.

The points numbers 301 through 382 in FIG. 15 represent breath luminescence measurements on patients having a variety of conditions, some of which are characterized by lung inflammation, and some of which are not. In the following table, the measurements are divided into groups, and each measurement is designated by a number corresponding to a point on the graph in FIG. 15. A brief description of each case is given.

301-310: Sarcoidosis Patients 305, 306, 308 and 310—untreated or early in treatment
309—remeasurement of 10 after treatment

311-322: Asthmatics 311, 312—no anti-inflammatory (prednisone) several other pulmonary diseases before and after spirometry (poor effort)
313—also has chronic obstructive pulmonary disease—no anti-inflammatory treatment
314—steroids
315—also has chronic bronchiectasis
316—acute attack earlier that day—high dose
317—acute attack in progress, just treated with high dose prednisone
318—acute attack in progress—prednisone treated
319—four months pregnant—prednisone treated
320—asthma and allergic bronchopulmonary aspergillosis steroid treated
321—allergic rhinitis control—not prednisone treated
322—acute attack in progress—prednisone treated

323-354: Lung Cancer

323—prednisone
324—no drugs
325—no drugs
326—lung CA removed—chest wall still active
327—lung CA surgically removed and post op radiation-receiving experimental drug WR 2721
328—non-oat-cell bronchogenic carcinoma—successfully surgically treated
329—non lung control (mandibular carcinoma pre O$_2$ therapy)
330—suspected cancer of unknown location
331—same patient as above—pre O$_2$ therapy
332—same patient as above—pre O$_2$ therapy 333—pulmonary resection two months prior (surgical removal of Pancoast tumor) and radiation therapy one month prior—successful
334—immediately after radiation therapy of active tumor
335—active adenocarcinoma with metastases to right scapula
336—active tumor, active asthma
337—large mediastinal tumor surgically removed
338—active tumor, smoker
339—active right upper lobe 340-354: Bis Chloro Nitroso Urea Treated Glioma (Pulmonary Toxin)

340—pre infusion
341—post infusion
342—post infusion
343—post infusion
344—post infusion
345—pre infusion
346—post infusion
347—post infusion
348—post infusion
349—pre infusion
350—post infusion
351—post infusion
352—pre infusion
353—pre infusion
354—taking prednisone 355-372: Normals 355—3 hrs. and 7 hrs. sleep two prior nights
356—smoker
357—complained of back pressure
358—asthma history
359—3 hrs. sleep each of last two nights
360—complained of back pressure—6 hrs. sleep
361—head cold
362—no apparent reason for higher count—possible radiology machine interference
363—possible radiology machine interference
364—2 hrs. horseback/day
365—vitamins $B_6$, $B_{12}$, C, E—Alcohol—6 hrs. sleep
366—just ate ½ pizza
367—aspirin, vitamin C
368—smoker
369—control normal—10 min. after cigarette
370—post lavage
371—smoker
372—just ate ½ pizza 373-376: Miscellaneous 373—silicosis—asbestosis
374—black lung
375—black lung
376—pneumonia—lupus erythematosis 377-382: $O_2$ Therapy 377—50 prior $O_2$ treatments—pre-therapy
378—osteomyelitis—pre-therapy
379—same patient after $O_2$ therapy
380—chronic osteomyelitis—pre-therapy
381—pre-therapy
382—post therapy In the case of sarcoidosis, cases 305, 306, 308 and 310 represent patients who were either untreated or in the early stages of treatment. Three of these four patients, corresponding to measurements 305, 306 and 308, fall well above the control normal. Sarcoidosis is typically treated with steriods or immunosuppressive drugs, all of which would be expected to reduce inflammation. The measurements for all of the sarcoidosis patients who were in the later stages of treatment fell well below the control normal. Measurements 309 and 310 pertain to the same patient, and that patient's breath luminescence was substantially reduced after treatment.

In the case of the asthmatics represented by points 311 through 323, those patients who were measured while an asthma attack was in progress showed breath luminescence levels above the control normal, even though some had taken anti-inflammatory drugs to control the attack. Other patients, such as those represented by points 314 and 316, who had been taking anti-inflammatory drugs showed low breath luminescence levels. A few cases were complicated by other conditions or treatments.

As indicated previously, lung cancer is an anti-inflammatory condition, generally characterized by lower than normal breath luminescence levels. Patients such as those represented by points 323, 324, 325, 329, 330, 331, 332, 334, 335 and 339, all had breath luminescence readings lower than the control normal. Patients represented by points 326, 327, 328, 333 and 337, all of whom had higher than normal breath luminescence readings, had been treated surgically. In the cases of points 336, and 338, asthma and smoking may account for the higher than normal breath luminescence readings.

Treatment with bis chloro nitroso urea (BCNU) is known to produce inflammation. Points 340 through 344 represent measurements taken on a first patient. Points 345 through 348 represent measurements on a second patient, and points 349 through 351 represent measurements on a third patient. Successive measurements showed that treatment with BCNU generally produced an increase in breath luminescence.

With few exceptions, normal subjects who exhibited higher than normal breath luminescence measurements had insufficient sleep, or had an unusual condition or had recently engaged in some activity which could explain an abnormally high luminescence measurement.

The silicosis and black lung disease patients represented by points 373, 374 and 375, had long histories of inflammatory insult, and, as expected, showed low breath luminescence measurements.

The pneumonia patient, represented by point 376 showed a breath luminescence measurement much higher than normal.

The statistical effect of the measurements on oxygen therapy patients was practically nil. Additional measurements, not depicted in FIG. 15, were taken on athletes, who, because of their physical conditions, would be expected to resist inflammation. These athletes exhibited very low breath luminescence measurements.

The data represented by FIG. 15 indicates that there is a high degree of correlation between pulmonary inflammation and breath luminescence, and that breath luminescence measurement is useful in screening patients for diseases characterized by pulmonary inflammation.

As indicated above, the apparatus can be readily modified for the detection of internal tissue luminescence by endoscopic means and for the measurement of luminescence of various samples in vitro. It can also be used to measure luminescence emitted externally by various body parts such as the hand. This can be accomplished by using collector 192 (FIG. 12) without receiver 196 and sample holder 198.

Numerous modifications can be made to the apparatus and procedure as described herein. For example, the gauze plug of FIG. 2 can be eliminated, provided that a special breathing tube is used with a tortuous passage or other means to prevent direct illumination of the photomultiplier by the luminescence of the patient's mouth tissues.

I claim:

1. A method of screening for pulmonary inflammation in a human patient comprising the steps of:
    measuring the quantity of light spontaneously emitted by the patient's breath; and
    comparing the quantity of light so measured with a preestablished standard for persons of the same age as the patient who are free of pulmonary inflammation, whereby if the quantity of light emitted by the patient's breath is substantially above the preestablished standard, the patient is considered a candidate for further diagnostic testing.

2. A method according to claim 1 in which the measuring step is carried out by means of an electronic light detector and in which light from sources other than the patient's breath is excluded from the light detector.

3. A method according to claim 2 in which the electronic light detector is a photon counter.

4. A method according to claim 1 in which the patient breathes into a chamber, light from all sources other than the patient's breath is excluded from the chamber, and the measuring step is carried out by measuring the quantity of light emitted by the patient's breath in said chamber.

5. A method according to claim 4 in which the measurement takes place while the patient exhales through the chamber, and the patient's breath exits from the chamber through a tortuous path.

6. A method according to claim 4 in which the patient breathes into the chamber through a tube and in which the patient is fitted with a light-proof mask extending from the tube to the patient's face, said mask having an upper opening fitting about the patient's face at approximately the level of the patient's nose, a lower opening, fitting about the patient's neck, and a front opening receiving the tube, said mask being fitted about the patient's face and neck and about the tube with sufficient tightness to prevent the entry of light from external sources into the tube.

7. A method according to claim 1 in which the patient breathes into a chamber, and light from all sources other than the patient's breath is excluded from the chamber, and the measuring step is carried out by photon counting.

* * * * *